US00PP08271P

United States Patent [19]

Dehan

[11] Patent Number: Plant 8,271

[45] Date of Patent: Jun. 22, 1993

[54] ASTER PLANT NAMED SUNROSE

[75] Inventor: Klara Dehan, Holon, Israel

[73] Assignee: Danziger — "Dan" Flower Farm, Mishmar Hashiva, Israel

[21] Appl. No.: 687,164

[22] Filed: Apr. 19, 1991

[51] Int. Cl.[5] ..... A01H 5/00
[52] U.S. Cl. ..... Plt./68.1
[58] Field of Search ..... Plt./68, 68.1

*Primary Examiner*—James R. Feyrer
*Attorney, Agent, or Firm*—Foley & Lardner

[57] ABSTRACT

An aster plant named Sunrose particularly characterized by its purple-violet ray floret color which does not fade on maturity; bushy habit with close internodes and sharply angular side branching; early flowering; prolific side branching; and by its one and one-half rows of ray florets.

1 Drawing Sheet

The present invention comprises a new and distinct cultivar of aster, botanically known as *Aster ericoides,* and hereinafter referred to by the cultivar name Sunrose.

The new cultivar was originated from a cross made by applicant in a controlled breeding program in Mishmar Hashiva, Israel. The female, or seed, parent was a cultivar designated 5-DDP-18. The male, or pollen, parent was a cultivar designated DPS.

Sunrose was discovered and selected by applicant as a flowering plant within the progeny of the stated cross in a controlled environment in Mishmar Hashiva, Israel. Asexual reproduction of the new cultivar by vegetative cuttings, as performed by applicant at Mishmar Hashiva, Israel, has demonstrated that the combination of characteristics as herein disclosed for the new cultivar are firmly fixed and retained through successive generations of asexual reproduction.

Sunrose has not been observed under all possible environmental conditions. The phenotype may vary significantly with variations in environment such as temperature, light intensity and day length. The following observations, measurements and comparisons describe plants grown in Mishmar Hashiva, Israel under conditions which closely approximate those generally used in commercial practice.

The following traits have been repeatedly observed and are determined to be basic characteristics of Sunrose which, in combination, distinguish this aster as a new and distinct cultivar:

1. The purple-violet ray floret color is unique, and the color does not fade with maturity.
2. The shape of the stem is different, being bushy with short intervals between internodes, and side branching at a very sharp angle (25°) to the stem.
3. Relatively early natural flowering date of Sep. 5–10.
4. Prolific side branching resulting in profuse flowering at certain periods of the year.
5. Single to double flower type, with 1.5 rows of ray florets.

The new cultivar can be compared to the cultivar Dark Pink Star, with the flower color of Sunrose being generally similar but somewhat darker than the color of Dark Pink Star. In addition, Sunrose is distinguished from Dark Pink Star by its larger number of petals, earlier flowering, and more flowering on its secondary branches.

Sunrose is also distinctive when compared with its parents. The female parent is generally characterized by its purple flower color, bushy stems and rich flowering. The male parent is characterized by its light purple flower color, tall growth habit and its productivity. The combined characteristics of Sunrose are clearly unexpected in view of the traits of its parents.

The accompanying color photographic drawings show a typical specimen plant of the new cultivar. The top photograph comprises a front perspective view of a section of a plant of Sunrose. The bottom photo comprises an enlarged closeup view of a single flower of Sunrose. The perspective view very accurately depicts flower and foliage color. In the closeup photograph, the ray florets are substantially more red-purple than the actual purple-violet ray floret color, but flower form and disc floret form and color are more clearly shown.

In the following description, color references are made to the Royal Horticultural Society Colour Chart (RHS), except where general colors of ordinary significance are referred to. Color values were taken under artificial light conditions at approximately noon on Jan. 20, 1991 at Mishmar Hashiva, Israel.

Botanical classification: *Aster ericoides* cv Sunrose.
Parentage:
*Male parent.*—DPS.
*Female parent.*—5-DDP-18.
Propagation: By stem cuttings, tissue culture and division.

INFLORESCENCE

A. Capitulum:
*Form.*—Generally flat.
*Type.*—Daisy.
*Diameter across face.*—2–2.5 cm.

B. Corolla of ray florets:
*Color (general tonality from a distance of three meters).*—Purple.
*Color (upper surface).*—80A.
*Color (under surface).*—88C.
*Number of ray florets.*—28–30, appearing in 1.5 rows, thereby giving the flower an appearance between single and double forms.

C. Corolla of disc florets:
*Color (mature).*—Light yellow.
*Color (immature).*—Yellow.
*Diameter of disc.*—0.7–0.8 cm.

D. Reproductive organs:

*Androecium.*—A single anther 2 mm in length and yellow 1D in color; pollen is yellow.

*Gynoecium.*—Style is approximately 3 mm in length and yellow 1D in color.

E. Flowering season: Natural flowering in Israel is early, occurring approximately Sep. 5–10. In photoperiodically controlled programs, flowering occurs after only five weeks of short days following four weeks of long days.

PLANT

A. General appearance: Generally bushy habit, with medium tall stems. Quantity of flowering on secondary branches depends on season of the year, with flowering being greatest in the summer.

B. Height: Medium tall, with height at commencement of flowering being 80–90 cm, based on short day control as above described.

C. Foliage:

*Color.*—137A-B.

*Shape.*—Long and narrow; typical leaf is approximately 13 cm long and 1.3 cm wide.

I claim:

1. A new and distinct cultivar of aster plant named Sunrose, as illustrated and described.

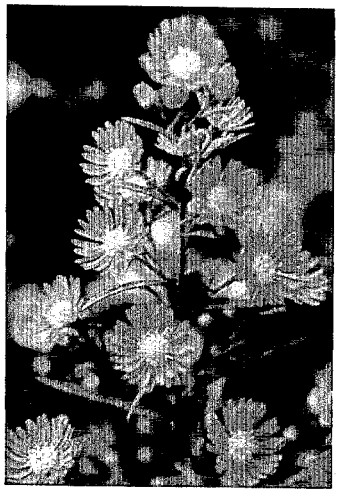
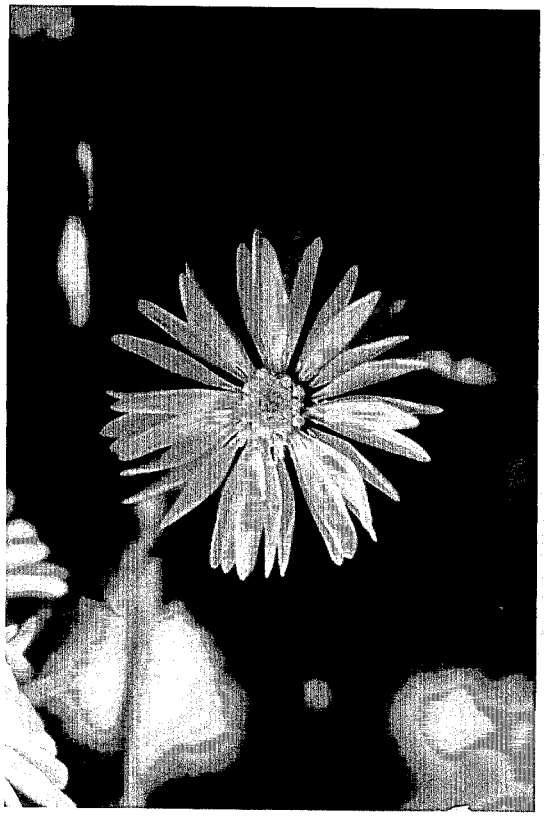

* * * * *